(12) United States Patent
Markert et al.

(10) Patent No.: US 7,476,647 B2
(45) Date of Patent: Jan. 13, 2009

(54) ETHER LACTONE

(75) Inventors: Thomas Markert, Monheim (DE); Alfred Westfechtel, Hilden (DE); Volker Porrmann, Hilden (DE)

(73) Assignee: Kao Corporation, Tokyo (JP)

( * ) Notice: Subject to any disclaimer, the term of this patent is extended or adjusted under 35 U.S.C. 154(b) by 619 days.

(21) Appl. No.: 10/507,372

(22) PCT Filed: Feb. 17, 2003

(86) PCT No.: PCT/EP03/01562

§ 371 (c)(1), (2), (4) Date: Apr. 28, 2005

(87) PCT Pub. No.: WO03/082851

PCT Pub. Date: Oct. 9, 2003

(65) Prior Publication Data

US 2005/0227908 A1    Oct. 13, 2005

(30) Foreign Application Priority Data

Mar. 28, 2002 (DE) .................... 102 13 899

(51) Int. Cl.
*A61K 8/18* (2006.01)
*A61Q 13/00* (2006.01)
*C07D 493/00* (2006.01)
*C07D 407/00* (2006.01)
*C07D 305/00* (2006.01)
*C07D 313/00* (2006.01)
*C07D 321/00* (2006.01)
*C07D 323/00* (2006.01)

(52) U.S. Cl. .......................... 512/12; 512/11; 549/263; 549/266; 549/267

(58) Field of Classification Search .................. 512/25, 512/11, 12; 549/267
See application file for complete search history.

(56) References Cited

U.S. PATENT DOCUMENTS 5,994,291 A   11/1999  Aida et al.
6,573,391 B1 *  6/2003  Eh et al. ..................... 549/267

OTHER PUBLICATIONS

Wright, R.H., "The Musk Odour", Perfumery and Essential Oil Record, vol. 58, No. 9, pp. 648-650, XP008017465 1967.
Sawant et al, J. Chem. Soc., Perkin Trans., 1999, vol. 1, pp. 2537-2542.
Chemistry Rules, 2006, pp. 1-20, accessed at http://www.rjclarkson.demon.co.uk.
Marszaleck et al, PNAS, USA (1999), vol. 96, pp. 7894-7898.
Alvarez-Larena, Acta. Cryst. (1995), vol. C51, pp. 1314-1319.
Linda Buck, "Unraveling the Sense of Smell", Nobel Lecture, Dec. 8, 2004, obtained from http://www.hhmi.org/research/nobel/buck.html, accessed Mar. 13, 2008).
The Merck Index, 12$^{th}$ Ed., 1996, p. 308.

* cited by examiner

*Primary Examiner*—Mark Eashoo
*Assistant Examiner*—Melissa Winkler
(74) *Attorney, Agent, or Firm*—Oblon, Spivak, McClelland, Maier & Neustadt, P.C.

(57) ABSTRACT

The invention relates to the ether lactone of formula (I) which is characterized by interesting and original odor characteristics, which diffuses extremely well and is suitable for use as a fragrance, for example in cosmetic preparations, technical products or in alcoholic perfumery.

3 Claims, No Drawings

ETHER LACTONE

FIELD OF THE INVENTION

The present invention relates to an ether lactone of a specific structure and its use as a fragrance.

PRIOR ART

Many natural fragrances, relative to their demand, are available in completely insufficient quantities. For example, 5,000 kg of rose petals are needed to produce 1 kg of rose oil. The consequences include a greatly limited annual production worldwide and a high price. It is therefore apparent that the fragrance industry has a constant need for new fragrances that exhibit interesting scents. On the one hand, the range of naturally available fragrances can be supplemented thereby, on the other hand it is thus possible to make the necessary adaptations to the ever-changing fashion in taste. Furthermore, this makes it possible to meet the ever-increasing demand for scent enhancers for products of daily use, such as cosmetics and cleaning agents.

Moreover, there is generally a constant demand for synthetic fragrances that can be produced inexpensively and with a uniform high quality, and which have the original olfactory characteristics. In particular, they are intended to exhibit pleasant, sufficiently intense scent profiles that are as natural as possible and are novel in terms of their quality. Such synthetic fragrances are also intended to be capable of beneficially influencing the scent of cosmetics and goods of daily use. In other words, there is a constant demand for compounds that exhibit characteristic novel scent profiles while simultaneously ensuring considerable staying power, intensity of scent and strong diffusion.

Perf. Essent. Oil Rec. 1967, 58(9), pages 648-650, in FIG. 1 on page 648, column 5, line 5 of the table, lists an ether lactone that exhibits an "average" musky scent and which is described in more detail by way of a formula.

DESCRIPTION OF THE INVENTION

It was found that the ether lactone of general formula (I) superlatively meets the aforementioned requirements in every way and that it can be advantageously used as a fragrance exhibiting diverse nuanced scents that in turn offer good staying power.

The subject matter of the present invention is, initially, the ether lactone of general structure (I)

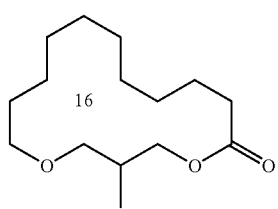

(I)

The invention further relates to the use as a fragrance of the ether lactone of general structure (I) described above in detail.

Compound (I) is characterized by an odour characteristic in which a musky quality dominates. Apart from an intense musky quality, scent aspects stand out that can be described as sweetish, redolent of balsam, with waxy qualities. (I) has excellent stability in formulations for cosmetics and perfumes of daily use.

Compound (I) may be produced on the basis of synthesizing techniques known in organic chemistry.

In perfume compositions, compound (I) enhances harmony and emanation as well as naturalness and staying power. Dosage is tailored to whichever scent is being striven for, while taking the composition's other constituents into account.

It was not foreseeable that compound (I) would exhibit the aforementioned scents, which provides further confirmation of the general experience that the olfactory characteristics of known fragrances do not permit automatic conclusions regarding the properties of structurally related compounds, since neither the mechanism of scent perception nor the effect of the chemical structure on scent perception have been adequately researched and since it therefore cannot normally be predicted as to whether a modified structure of known perfumes actually causes the olfactory characteristics to be modified or as to whether these modifications are assessed positively or negatively by the person skilled in the art.

Attention must be explicitly drawn to the fact that the scent characteristic of compound (I) according to the invention differs clearly from the ether lactone that exhibits merely an "average" musky scent and which is described in more detail by way of a formula in Perf. Essent. Oil Rec. 1967, 58(9), pages 648-650, in FIG. 1 on page 648, column 5, line 5 of the table. As far as the person skilled in the art was concerned, it was therefore neither foreseeable nor evident—on the basis of the structure mentioned in Perfum. Essent. Oil Rec. 1967, 58(9), pages 648-650, in FIG. 1 on page 648, column 5, line 5, and as a result of the introduction of a methyl substituent at an entirely specific position—to arrive at a compound that exhibits a much more intense musk scent with additional further scent qualities.

Owing to its scent profile, the formula (I) compound is, furthermore, particularly suitable for modifying and enhancing known compositions. Particular emphasis should be placed on its outstanding intensity of scent, which contributes, in a quite general way, toward the composition's refinement.

The formula (I) compound can be combined with numerous known fragrance ingredients, such as other perfumes of a natural, synthetic or partially synthetic origin, essential oils and plant extracts. The range of natural fragrances may include components that are both readily volatile as well as ones that exhibit medium and low volatility. The range of synthetic fragrances may include representatives of virtually any substance class.

Examples of suitable substances with which compound (I) can be combined include in particular:

(a) Natural products such as evemia furfuraceae (tree moss) absolute, basilicum oil, citrus oils such as bergamot oil, mandarin oil, etc., mastic absolute, myrtle oil, palmarosa oil, patchouli oil, petit grain oil, absinth oil, myrrh oil, olibanum oil, cedar wood oil, sandal wood oil, East Indian, guajak wood oil, cabreuva, (b) Alcohols such as famesol, geraniol, citronellol, linalool, nerol, phenylethyl alcohol, rhodinol, cinnamyl alcohol, Sandalore [3-methyl-5-(2.2.3-trimethylcyclopent-3-en-1-yl)pentan-2-ol], Sandela [3-isocamphyl-(5)-cyclohexanol], Mugetanol, (c) Aldehydes such as citral, Helional®, alpha-hexylcinnamaldehyde, hydroxycitronellal, Lilial® [p-tert.-butyl-α-methyldihydrocinnamaldehyde], methylnonylacetaldehyde, (d) Ketones such as allyl ionone, α-ionone, β-ionone, Isoraldein, methyl ionone, noot katone, Calone, α-, β- and γ-irones, damascone, (e) Esters such as allyl phenoxyacetate, benzylsalicylate, cinnamylpropionate, citronellyll acetate, decylacetate, dimethylbenzylcarbinylacetate, ethylacetoacetate, hexenylisobutyrate, linalylacetate, methyldihydrojasmonate, vetiverylacetate, cyclohexylsalicylate, isobornylisobutyrate, evernyl, (f) Lactones such as gamma-undecalactone, 1-oxaspiro[4.4]nonan-2-one, cylopentadecanolide, ethylene brassylate, (g) Ethers such as Herbavert, ambroxan, as well as various further components often used in the perfume industry such as musk and sandal wood fragrances, indole, p-menthane-8-thiol-3-one, methyleugenol and methylanthranilate.

Noteworthy is, furthermore, how the structure (I) compound rounds off the scents of a wide range of known compositions and harmonizes these without, however, being dominant in an unpleasant manner.

The usable proportions of compound (I) in fragrance compositions range from approximately 1-70% by weight, based on the entire mixture. Compound (I) and fragrance compositions that contain compound (I) can be used both to perfume cosmetic preparations, such as lotions, creams, shampoos, soaps, ointments, powders, aerosols, toothpastes, mouthwash and deodorants, as well as in alcoholic perfumery (e.g. eau de cologne, eau de toilette, extracts). There is also the possibility to use the aforementioned to perfume technical products such as detergents and cleaning agents, fabric softeners and textile treating agents. To perfume these various products, the compositions are added thereto in an amount effective olfactorily, in particular in a concentration of 0.01 to 2% by weight, based on the entire product. These values do not, however, constitute limits since the experienced perfumer can still attain effects with even lesser concentrations or can construct novel complexes with even higher dosages.

EXAMPLES

Example 1

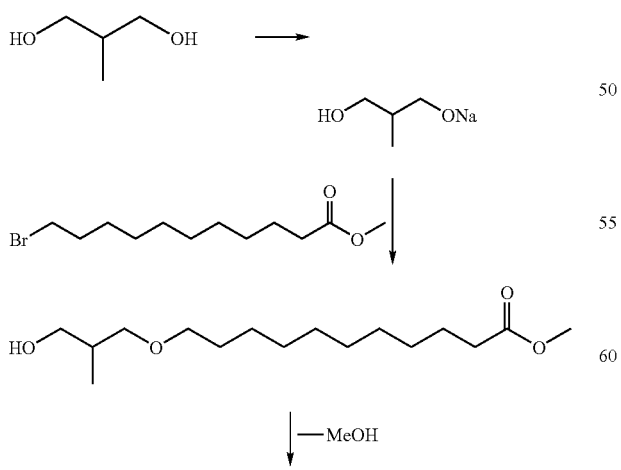

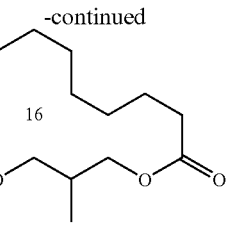

90 g (1 mol) 2-methylpropane-1,3-diol and 27 g (0.5 mol) sodium methylate were suspended in 200 ml xylene and heated to reflux temperature in a water trap at 140° C. for 24 hours while being stirred vigorously. Then, 99 g (0.35 mol) methyl 11-bromoundecanoate was continuously added dropwise to the mixture over approx. 3 hours at 140° C. and refluxed for another 3 hours. Afterward, the gas chromatogram still showed approx. 25-% unconverted methyl bromoundecanoate. 90 g sodium methylate (30% in methanol) and 10 g polyethylene glycol 600 were added and heated for another 4 hours at 132° C. in the water trap, whereby methanol was removed by distillation.

Further Processing:

The reaction mixture was concentrated, the 80 g crude product thus obtained was slowly distilled over on a bulb tube distiller. 20 g 30-% product and 20.2 g 75-% material were trapped as fractions.

Analysis:

The IR spectrum (ATR technique) showed characteristic bands at 1112, 1174, 1248, 1733 $cm^{-1}$ and a vibrational CH range from 2858 to 2929 $cm^{-1}$.

The $^1$H-NMR spectrum (400 MHz in $CDCl_3$) showed 1 methyl group (2 singlets, 3H) at 0.95 ppm. A signal peak at 1.3 ppm corresponds to 5 $CH_2$ groups, 2 broad signals at 1.6 and 1.7 ppm correspond to 3 $CH_2$ groups, and one signal at 2.3 ppm corresponds to 1 $CH_2$ group. The signal at 2.0 ppm is assigned to the CH at which the methyl group is positioned. A signal mixture that had been split up in a complex fashion was located in the range from 3.3. to 4.2 ppm; this corresponds to 3 $CH_2$ groups in the vicinity of the oxygen atoms in the ring.

Scent Characteristic:

When first smelled, typically musk, sweetish, redolent of balsam, with waxy qualities and ones such as a hot domestic iron; after 24 hours on the scent strip, the subsequent smell was redolent of musk, warm wax; this scent remained for several weeks.

The invention claimed is:

1. An ether lactone of formula (I)

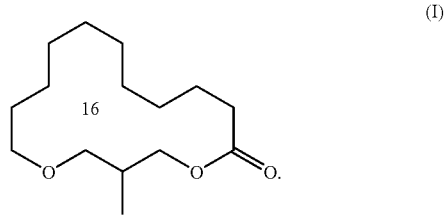

2. A fragrance composition comprising an ether lactone of formula (I)

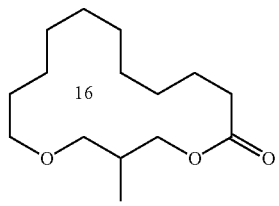

(I)

wherein said ether lactone is present in an amount of 1 to 70% by weight, based on the entire composition.

3. The fragrance composition according to claim 2, further comprising at least one ingredient selected from the group consisting of essential oils, alcohols, plant extracts, aldehydes, ketones, esters, ethers, lactones differing from the ether lactone of formula (I), sandal wood fragrances, indole, p-menthane-8-thiol-3, methyleugenol, and methylanthranilate.

* * * * *